United States Patent
Stoltefuss et al.

Patent Number: 5,017,590
Date of Patent: May 21, 1991

[54] 1,4-DIHYDROPYRIDINE-THREONINE COMPOUNDS WITH CARDIOVASCULAR ACTIVITY

[75] Inventors: Jürgen Stoltefuss, Haan; Martin Bechem, Wuppertal; Rainer Gross, Wuppertal; Siegbert Hebisch, Wuppertal; Matthias Schramm, Cologne, all of Fed. Rep. of Germany

[73] Assignee: Bayer Aktiengesellschaft, Leverkusen, Fed. Rep. of Germany

[21] Appl. No.: 367,408

[22] Filed: Jun. 15, 1989

[30] Foreign Application Priority Data

Jun. 24, 1988 [DE] Fed. Rep. of Germany ....... 3821334

[51] Int. Cl.$^5$ ................ C07D 211/90; A61K 31/455
[52] U.S. Cl. ...................................... 514/356; 546/321
[58] Field of Search ................ 546/322, 321; 514/356

[56] References Cited

FOREIGN PATENT DOCUMENTS 0742737 6/1970 Belgium ............................. 546/322
3244178 5/1984 Fed. Rep. of Germany ...... 546/322

OTHER PUBLICATIONS

Chemical Abstracts, vol. 109, No. 11, Abstract 92803j, Sep. 12, 1988, p. 690, Nakajima et al.
Chemical Abstracts, vol. 110, No. 9, Abstract 75331g, Feb. 27, 1989, p. 634, Nakajima et al.

Primary Examiner—Frederick E. Waddell
Assistant Examiner—Zinna Northington-Davis
Attorney, Agent, or Firm—Sprung Horn Kramer & Woods

[57] ABSTRACT

Cardioactive dihydropyridines of the formula

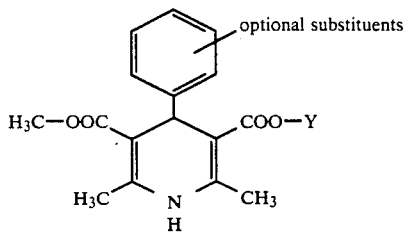

in which
Y is

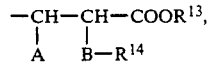

A is H or $CH_3$,
B is —NH, —NH—CO—, —NH—CS—, —NH—COO—, —NH—$SO_2$— or —NH—CO—NH— or —NH—CS—NH—, and
$R^{13}$ and $R^{14}$ each independently is H or an organic radical, and salts thereof. The Y can be hydrolyzed off. The other radicals on the dihydropyridine moiety can also be varied.

6 Claims, No Drawings

1,4-DIHYDROPYRIDINE-THREONINE COMPOUNDS WITH CARDIOVASCULAR ACTIVITY

The present invention relates to new dihydropyridine derivatives and processes for their preparation via new intermediates in their use in the medical field.

It has already been disclosed that dihydropyridinecarboxylic acids can be prepared from the corresponding dihydropyridinecarboxylic acid β-cyanoethyl esters cf. DOS (German Published Specification) No. 3,929,545.

The invention relates to dihydropyridine derivatives of the formula (I)

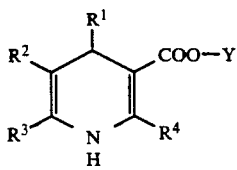

(I)

in which
R$^1$ stands for straight-chain or branched alkyl having up to 6 carbon atoms which is optionally substituted by halogen, hydroxyl, C$_1$-C$_8$-alkoxy, carboxyl, C$_1$-C$_8$-alkoxycarbonyl or phenyl, or
stands for cycloalkyl having 3 to 6 carbon atoms, or stands for aryl having 6 to 10 carbon atoms which is monosubstituted, disubstituted or trisubstituted by identical or different nitro, cyano, C$_1$-C$_6$-halogenoalkyl, halogen, C$_1$-C$_6$-alkyl or C$_1$-C$_6$-alkoxycarbonyl, or by C$_1$-C$_6$-halogenoalkoxy, C$_1$-C$_4$-halogenoalkylthio, carbamoyl, dialkylcarbamoyl having up to 6 carbon atoms per alkyl group, or C$_2$-C$_8$-alkenyl which can optionally be substituted by C$_1$-C$_6$-alkoxycarbonyl, or by phenylsulphonyloxy which is optionally substituted by C$_1$-C$_6$-alkyl, C$_1$-C$_6$-alkoxy, nitro, halogen, cyano, C$_1$-C$_4$-halogenoalkyl or C$_1$-C$_4$-halogenoalkoxy, or by C$_1$-C$_8$-alkylamino or dialkylamino each having up to 6 carbon atoms per alkyl group, or C$_1$-C$_8$-acylamino, or by C$_1$-C$_8$-alkoxy or C$_1$-C$_8$-alkylthio, each of which can optionally be substituted by cyclohexyl or phenyl which, in turn, can be substituted by halogen, C$_1$-C$_6$-alkyl, C$_1$-C$_6$-alkoxy, nitro, C$_1$-C$_4$-halogenoalkyl, C$_1$-C$_2$-alkoxycarbonyl, cyano or C$_1$-C$_4$-halogenoalkoxy, or
stands for a mono-, bi- or tricyclic, saturated or unsaturated heterocycle which can contain up to 3 hetero atoms from the group N, O or S and which can be substituted by C$_1$-C$_4$-alkylthio,
R$^2$ stands for nitro, cyano or halogen, or
stands for straight-chain or branched alkyl having up to 12 C atoms, or
stands for phenyl which can be substituted by nitro, cyano, halogen, C$_1$-C$_6$-alkyl, C$_1$-C$_6$-alkoxy, C$_1$-C$_6$-alkylthio, trifluoromethyl, trifluoromethoxy, difluoromethoxy or trifluoromethylthio,
stands for a group of the formula

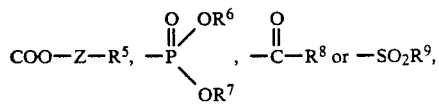

wherein
R$_5$ stands for hydrogen, or
stands for a straight-chain, branched on cyclic, saturated or unsaturated hydrocarbon radical having up to 12 C atoms which can be interrupted by an oxygen or sulphur atom and which can be substituted by N$_3$, hydroxyl, nitro, halogen, C$_1$-C$_6$-acyloxy, carboxyl, C$_1$-C$_6$-alkoxycarbonyl, CN or C$_1$-C$_8$-acyl, or by phenyl or phenoxy which are optionally substituted by halogen, C$_1$-C$_4$-alkyl, C$_1$-C$_4$-alkoxy or C$_1$-C$_2$-halogenoalkyl, or
stands for a radical

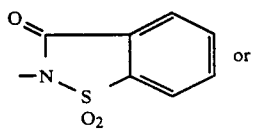 or stands for a group of the formula

wherein
R$^{10}$ and R$^{11}$ are identical or different and
stand for hydrogen, for straight-chain or branched alkyl having up to 8 carbon atoms and which can be substituted by halogen, hydroxyl, alkoxy having up to 6 carbon atoms, carboxyl or alkoxycarbonyl having up to 10 carbon atoms, or by phenyl which is optionally substituted by trifluoromethyl, trifluoromethoxy, alkyl having up to 6 carbon atoms, halogen or alkoxy having up to 6 carbon atoms, or
stand for cycloalkyl having 3 to 8 carbon atoms, or
stand for phenyl which can be substituted by identical or different halogen, alkyl having up to 6 carbon atoms, alkoxy having up to 6 carbon atoms, alkylthio having up to 4 carbon atoms, trifluoromethyl, trifluoromethoxy, difluoromethoxy, trifluoromethylthio, amino, alkylamino having up to 8 carbon atoms or dialkylamino in each case having up to 8 carbon atoms per alkyl group,
or R$^{10}$ and R$^{11}$, together with the nitrogen atom, form a 5- to 7-membered saturated or unsaturated heterocyclic ring which can contain an oxygen atom, a sulphur atom or a nitrogen atom as an additional hetero atom which can optionally be substituted by a radical R$^{12}$,
wherein
R$^{12}$ stands for hydrogen, a straight-chain or branched, saturated or unsaturated alkyl group having up to 4 carbon atoms which can be substituted by phenyl which, in turn, is substituted by halogen, alkyl having up to 4 C atoms, alkoxy having up to 4 C atoms, nitro and halogenoalkyl having up to 4 C atoms, or stands for phenyl which is optionally substituted by halogen, cyano, nitro, alkyl having up to 4 C atoms or halogenoalkyl having up to 4 C atoms, and
Z denotes a single bond or a straight-chain or branched alkylene chain having up to 10 C atoms, and
R$^6$ and R$^7$ can be identical or different and stand for hydrogen or $C_1$-$C_6$-alkyl, or, together with the oxygen atoms, form a 5-membered ring via an ethylene bridge, and $R^8$ stands for straight-chain or branched alkyl having up to 10 carbon atoms, or stands for a radical

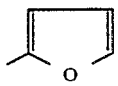

or stands for the group

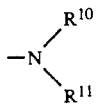

wherein $R^{10}$ and $R^{11}$ have the abovementioned meaning, and $R^9$ stands for straight-chain or branched alkyl having up to 8 carbon atoms, or stands for phenyl which can be substituted by nitro, cyano, halogen, alkyl having up to 2 carbon atoms, alkoxy having up to 2 carbon atoms, trifluoromethyl, trifluoromethoxy or difluoromethoxy, and $R^3$ stands for straight-chain, branched or cyclic alkyl having up to 6 carbon atoms which is optionally substituted by hydroxyl, cyano, phenyl, halogeno or aminoethoxy, or stands for cyano, or $R^2$ and $R^3$ jointly form a saturated or unsaturated 5- to 7-membered ring which can optionally contain up to 3 identical or different ring members from the group comprising =CH—, —CH$_2$—, O, CO, CS, S or —N=, and $R^4$ stands for straight-chain or branched alkyl or alkenyl having up to 12 carbon atoms and which can optionally be substituted by halogen, hydroxyl, $C_1$-$C_6$-alkoxy, trifluoromethyl, carboxyl, $C_1$-$C_6$-alkoxycarbonyl or phenyl which can be substituted by nitro, halogen, $C_1$-$C_2$-alkyl, $C_1$-$C_4$-alkoxy, trifluoromethyl or trifluoromethoxy, or stands for cycloalkyl having 3 to 8 carbon atoms, or stands for phenyl which can optionally be substituted by nitro, halogen, $C_1$-$C_2$-alkyl or $C_1$-$C_4$-alkoxy, and Y stands for a radical

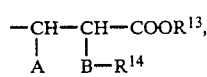

wherein

A stands for hydrogen or methyl, and

B stands for a group of the formula —NH, —NH—CO—, —NH—CS—, —NH—COO—, —NH—SO$_2$— or —NH—CO—NH— or —NH—CS—NH—, $R^{13}$ stands for hydrogen, or stands for straight-chain or branched alkyl having up to 12 carbon atoms and which can be substituted by halogen, hydroxyl, carboxyl, cyano, $C_1$-$C_8$-alkoxycarbonyl, carbonyl, alkylamino or dialkylamino having up to 8 carbon atoms, carbamoyl, $C_1$-$C_6$-alkoxy or phenyl which can be substituted by nitro, cyano, trifluoromethyl, trifluoromethoxy, halogen, $C_1$-$C_6$-alkoxy or $C_1$-$C_2$-alkyl, or stands for cycloalkyl having 3 to 8 carbon atoms, or stands for phenyl which can be substituted by halogen, $C_1$-$C_3$-alkyl, $C_1$-$C_3$-alkoxy, $C_1$-$C_3$-halogenoalkyl or $C_1$-$C_3$-halogenoalkoxy, $R^{14}$ stands for hydrogen, or stands for straight-chain or branched alkyl or alkenyl each having up to 12 carbon atoms and which can be substituted by halogen, hydroxyl, $C_1$-$C_8$-alkoxy, nitro, cyano, $C_1$-$C_8$-alkylthio, carboxyl, $C_1$-$C_8$-alkoxycarbonyl or phenyl which can be substituted by nitro, cyano, trifluoromethyl, trifluoromethoxy, $C_1$-$C_8$-alkyl, halogen or $C_1$-$C_8$-alkoxy, or stands for cycloalkyl having 3 to 8 carbon atoms, or stands for aryl having 6 to 10 carbon atoms which can be monosubstituted to pentasubstituted by identical or different nitro, cyano, halogen, $C_1$-$C_8$-alkyl, $C_1$-$C_8$-alkoxy, $C_1$-$C_8$-alkylthio, carbamoyl or dialkylcarbamoyl in each case having up to 6 carbon atoms per alkyl group, carboxyl, $C_1$-$C_8$-alkoxycarbonyl, $C_1$-$C_6$-halogenoalkyl, $C_1$-$C_6$-halogenoalkoxy, $C_1$-$C_6$-halogenoalkylthio, $C_1$-$C_6$-alkylsulphonyl, $C_1$-$C_6$-alkylsulphamoyl, amino, $C_1$-$C_8$-alkylamino or dialkylamino in each case having up to 8 carbon atoms per alkyl group or $C_1$-$C_8$-acylamino, or stands for a 5- to 7-membered saturated or unsaturated, heterocyclic ring which can contain one to three oxygen, sulphur and/or nitrogen atoms as hetero atoms, and their physiologically acceptable salts.

The compounds according to the invention exist in stereoisomeric forms which either behave as image and mirror image (enantiomers) or which do not behave as image and mirror image (diastereomers). The invention relates both to the antipodes and the racemic forms and also the mixture of diastereomers. The racemic forms can be resolved, just like the diastereomers, into the stereoisomerically uniform constituents in a known manner (cf. E. L. Eliel, Stereochemistry of Carbon Compounds, McGraw Hill, 1962).

Physiologically acceptable salts may be salts of the compounds according to the invention with inorganic or organic acids or bases. Salts with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid or benzoic acid, or methanesulphonic acid, ethanesulphonic acid, phenylsulphonic acid, toluenesulphonic acid or naphthalenedisulphonic acid and salts with bases such as, for example, sodium hydroxide, potassium hydroxide, barium hydroxide or ammonium salts, or salts with organic bases such as pyridine or triethylamine are preferred.

Preferred compounds of the general formula (I) are those in which $R^1$ stands for straight-chain or branched alkyl having up to 4 carbon atoms which can optionally be substituted by phenyl, $C_1$-$C_2$-alkoxycarbonyl or carboxyl, or stands for phenyl which can be monosubstituted, disubstituted or trisubstituted by identical or different nitro, cyano, $C_1$-$C_4$-halogenoalkyl, halogen, $C_1$-$C_4$-alkyl, $C_1$-$C_4$-alkoxycarbonyl, $C_1$-$C_2$-halogenoalkoxy, $C_1$-$C_2$-halogenoalkylthio or $C_1$–$C_4$-alkoxycarbonyl, or by phenylsulphonyloxy which is optionally substituted by $C_1$–$C_2$-alkyl or halogen, or by $C_1$–$C_4$-alkoxy or $C_1$–$C_4$-alkylthio, each of which can be substituted by cyclohexyl or phenyl which can optionally be substituted by halogen, $C_1$–$C_4$-alkyl, $C_1$–$C_4$-alkoxy, nitro, $C_1$–$C_4$-halogenoalkyl, cyano or $C_1$–$C_4$-halogenoalkoxy, or stands for a mono- or bicyclic unsaturated heterocycle which can contain up to 3 hetero atoms from the group comprising N, O or S, and which can optionally be substituted by $C_1$–$C_3$-alkylthio, and $R^2$ stands for nitro or cyano, or stands for straight-chain or branched alkyl having up to 6 carbon atoms, or stands for phenyl which can be substituted by nitro, cyano, halogen, $C_1$–$C_2$-alkyl, $C_1$–$C_2$-alkoxy or trifluoromethyl, or stands for a group of the formula

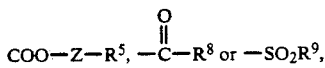

$COO-Z-R^5$, $-\overset{O}{\overset{\|}{C}}-R^8$ or $-SO_2R^9$, wherein $R^5$ stands for hydrogen, or stands for a straight-chain, branched or cyclic, saturated or unsaturated hydrocarbon radical having up to 8 carbon atoms and which can be interrupted by an oxygen or sulphur atom and which can be substituted by hydroxyl, nitro, halogen, $C_1$–$C_6$-alkoxycarbonyl or carboxyl, or by phenyl or phenoxy which are optionally substituted by halogen or $C_1$–$C_2$-alkyl or $C_1$–$C_2$-alkoxy, or stands for a group of the formula

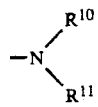

wherein $R^{10}$ and $R^{11}$ are identical or different and stand for hydrogen, or stand for straight-chain or branched alkyl having up to 8 carbon atoms and which can be substituted by hydroxyl, alkoxy having up to 4 carbon atoms, carboxyl or alkoxycarbonyl having up to 8 carbon atoms, or by phenyl which is optionally substituted by trifluoromethyl, trifluoromethoxy, alkyl having up to 4 carbon atoms, halogen or alkoxy having up to 4 carbon atoms, or stands for cycloalkyl having 3 to 6 carbon atoms, or stands for phenyl which can be substituted by halogen, alkyl having up to 4 carbon atoms, alkoxy having up to 4 carbon atoms, alkylthio having up to 4 carbon atoms, trifluoromethyl, trifluoromethoxy or difluoromethoxy, or $R^{10}$ and $R^{11}$, together with the nitrogen atom, form a 5- to 7-membered saturated heterocyclic ring which can contain an oxygen atom, a sulphur atom or a nitrogen atom as an additional hetero atom, which can be substituted by a radical $R^{12}$, wherein $R^{12}$ stands for hydrogen, an alkyl group having up to 4 carbon atoms which is optionally substituted by phenyl which, in turn, can be substituted by halogen, $C_1$–$C_2$-alkyl, $C_1$–$C_2$-alkoxy or $C_1$–$C_2$-halegenoalkyl, or stands for phenyl which can optionally be substituted by halogen, $C_1$–$C_2$-alkyl or $C_1$–$C_2$-halogenoalkyl, Z denotes a single bond or a straight-chain or branched alkylene chain having up to 8 C atoms, and $R^8$ stands for straight-chain or branched alkyl having up to 6 carbon atoms, or stands for the group

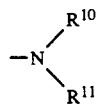

wherein $R^{10}$ and $R^{11}$ have the abovementioned meaning, and $R^9$ stands for straight-chain or branched alkyl having up to 4 carbon atoms, or stands for phenyl which can be substituted by halogen, $C_1$–$C_2$-alkyl, $C_1$–$C_2$-alkoxy, trifluoromethyl, trifluoromethoxy or difluoromethoxy, and $R^3$ stands for straight-chain, branched or cyclic alkyl having up to 6 carbon atoms which can be substituted by hydroxyl or aminoethoxy, or $R^2$ and $R^3$ jointly form a saturated or unsaturated 5- to 7-membered ring which can optionally contain up to 3 different ring members from the group comprising $=CH-$, $-CH_2-$, O, CO, CS, $-N=$ or S, and $R^4$ stands for straight-chain or branched alkyl having up to 6 carbon atoms which can be substituted by halogen, hydroxyl, carboxyl or $C_1$–$C_4$-alkoxycarbonyl, or can be substituted by phenyl which, in turn, can be substituted by halogen, $C_1$–$C_2$-alkyl, $C_1$–$C_2$-alkoxy, trifluoromethyl or trifluoromethoxy, or stands for cycloalkyl having 3 to 6 carbon atoms, or stands for phenyl which can optionally be substituted by halogen, $C_1$–$C_2$-alkyl or $C_1$–$C_2$-alkoxy and Y stands for a radical

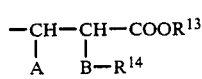

wherein

A stands for hydrogen or methyl and

B stands for a group of the formula $-NH$, $-NH-CO-$, $-NH-COO-$, $-NH-SO_2-$ or $-NH-CO-NH-$ and $R^{13}$ stands for hydrogen, or stands for straight-chain or branched alkyl having up to 8 carbon atoms which can be substituted by halogen, hydroxyl, $C_1$–$C_3$-alkoxy, trifluoromethyl, carboxyl, $C_1$–$C_6$-alkoxycarbonyl or phenyl which, in turn, can be substituted by trifluoromethyl, trifluoromethoxy, halogen, $C_1$–$C_3$-alkoxy or $C_1$–$C_2$-alkyl, or stands for cycloalkyl having 3 to 6 carbon atoms, or stands for phenyl which can be substituted by halogen, $C_1$–$C_2$-alkyl or $C_1$–$C_2$-alkoxy, and $R^{14}$ stands for hydrogen, or stands for straight-chain or branched alkyl or alkenyl each having up to 8 carbon atoms and which can be substituted by halogen, hydroxyl, $C_1$–$C_4$-alkoxy, cyano, $C_1$–$C_4$-alkylthio, carboxyl, $C_1$–$C_4$-alkoxycarbonyl or phenyl which, in turn, can be substituted by trifluoromethyl, trifluoromethoxy, $C_1$-$C_4$-alkyl, halogen or $C_1$-$C_4$-alkoxy, or stands for cycloalkyl having 3 to 6 carbon atoms, or stands for phenyl which can be monosubstituted or disubstituted by identical or different nitro, cyano, halogen, $C_1$-$C_4$-alkyl, $C_1$-$C_4$-alkoxy, $C_1$-$C_4$-alkylthio, carbamoyl, dialkylcarbamoyl having up to 4 carbon atoms per alkyl group, carboxyl, $C_1$-$C_6$-alkoxycarbonyl, $C_1$-$C_3$-halogenoalkyl, $C_1$-$C_3$-halogenoalkoxy, $C_1$-$C_3$-halogenoalkylthio, $C_1$-$C_3$-alkylsulphonyl, $C_1$-$C_3$-alkylsulphamoyl, amino, $C_1$-$C_4$-alkylamino or dialkylamino in each case having up to 4 carbon atoms per alkyl group or $C_1$-$C_4$-acylamino, or stands for a 5- to 6-membered unsaturated heterocyclic ring which can contain a nitrogen atom as a hetero atom, and their salts.

In the case in which $R^2$ and $R^3$ jointly form a saturated or unsaturated 5- to 7-membered ring which can optionally contain up to 3 different ring members from the group O, =CH—, —CH$_2$—, CO, CS, S, —NR$^{3'}$— or —N=, where $R^{3'}$ has the meaning of $R^3$, the radicals shown below are of particular interest

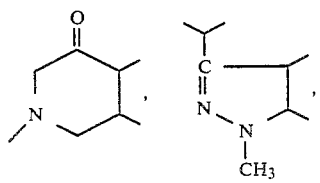

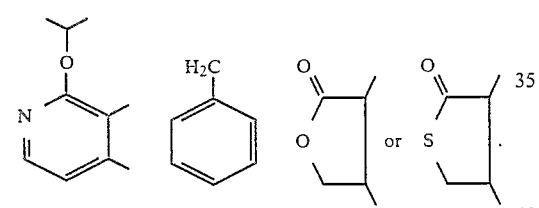

Particularly preferred compounds of the general formula (I) are those
in which
$R^1$ stands for straight-chain or branched alkyl having up to 4 carbon atoms, or stands for cyclopropyl, cyclopentyl or cyclohexyl, or stands for phenyl which can be monosubstituted or disubstituted by identical or different nitro, cyano, trifluoromethyl, fluorine, chlorine, methyl, methoxy, trifluoromethoxy, difluoromethoxy or phenylsulphonyloxy which is optionally substituted by methyl, fluorine or chlorine, or by $C_1$-$C_4$-alkoxy or $C_1$-$C_4$-alkylthio which can each be substituted by cyclohexyl or phenyl which, in turn, can be substituted by methyl, fluorine, chlorine or methoxy, or stands for pyridyl and $R^2$ stands for nitro, or for a group of the formula

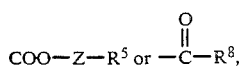

wherein
$R^5$ stands for hydrogen or $C_1$-$C_6$-alkyl which can optionally be interrupted by oxygen or sulphur and which can optionally be substituted by hydroxyl, $C_1$-$C_4$-alkoxycarbonyl or carboxyl, or by phenyl or phenoxy which is optionally substituted by fluorine, chlorine, methyl or methoxy, or stands for a group of the formula

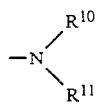

wherein
$R^{10}$ and $R^{11}$ are identical or different and each
stands for hydrogen, for straight-chain or branched alkyl having up to 6 carbon atoms and which can be substituted by fluorine, chlorine, hydroxyl, ethoxy, methoxy, carboxyl or $C_1$-$C_4$-alkoxycarbonyl, or by phenyl which, in turn, can be substituted by trifluoromethyl, trifluoromethoxy, $C_1$-$C_2$-alkyl, fluorine, chlorine or $C_1$-$C_2$-alkoxy, or stands for cyclopropyl, cyclopentyl or cyclohexyl, or stands for phenyl which can be substituted by fluorine, chlorine, $C_1$-$C_2$-alkyl, $C_1$-$C_2$-alkoxy, trifluoromethyl, trifluoromethoxy, difluoromethoxy, trifluoromethylthio, amino or $C_1$-$C_2$-alkylamino, or $R^{10}$ and $R^{11}$ together stand for piperidinyl, morpholinyl, methyl-piperazinyl or N-benzylpiperazinyl, and Z stands for a single bond or a straight-chain or branched alkylene chain having up to 6 C atoms and $R^8$ stands for straight-chain or branched alkyl having up to 4 carbon atoms, or stands for the group

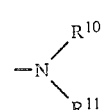

wherein
$R^{10}$ and $R^{11}$ have the abovementioned meaning, and
$R^3$ stands for straight-chain, branched or cyclic alkyl having up to 4 carbon atoms, or $R^2$ and $R^3$ jointly form a ring of the formula

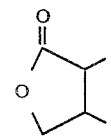

and
$R^4$ stands for straight-chain or branched alkyl having up to 4 carbon atoms, or stands for cyclopropyl, and Y stands for a radical

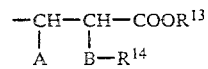

wherein
A stands for hydrogen or methyl, and
B stands for a group of the formula —NH—, —NH—CO—, —NH—COO—, —NH—SO$_2$— or —NH—CO—NH—, and $R^{13}$ stands for straight-chain or branched alkyl having up to 6 carbon atoms which can be substituted by hydroxyl, methoxy or phenyl, and $R^{14}$ denotes hydrogen, or stands for straight-chain or branched alkyl having up to 6 carbon atoms and which can be substituted by hydroxyl or $C_1$-$C_2$-alkoxycarbonyl, or by phenyl which, in turn, can be substituted by methyl, trifluoromethyl, fluorine or chlorine, or stands for cyclopropyl, cyclopentyl or cyclohexyl, or stands for phenyl which can be monosubstituted or disubstituted by identical or different nitro, cyano, fluorine, chlorine, $C_1$-$C_2$-alkyl, $C_1$-$C_4$-alkoxy, $C_1$-$C_2$-alkylthio, carbamoyl, carboxyl, $C_1$-$C_4$-alkoxycarbonyl, trifluoromethyl, trifluoromethoxy, $C_1$-$C_2$-alkylsulphamoyl or $C_1$-$C_2$-alkylamino, or stands for pyridyl, and their salts.

The compounds according to the invention are new and possess useful pharmacological properties. They influence the contractility of the heart and may therefore be used for the control of cardiovascular disorders. Owing to the possibility of preparing pure enantiomers, the desired pharmacological properties of the compounds can be expressed in different directions.

The compounds according to the invention of the general formula (I)

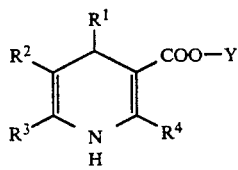

(I)

in which $R^1$, $R^2$, $R^3$, $R^4$ and Y have the abovementioned meaning, are obtained by means of the intermediates of the general formula (II)

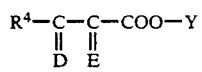

(IIa)

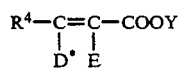

(IIb)

in which $R^4$ and Y have the abovementioned meanings,

D stands for oxygen or for the group NH,

D* stands for hydroxy or for the group $NH_2$ and

E stands for two hydrogens or for the group $=CHR^1$ in (IIa) or for one hydrogen in (IIb), wherein $R^1$ has the abovementioned meanings, by a process in which

[A] aldehydes of the general formula (III)

(III)

in which $R^1$ has the abovementioned meaning, and the compounds of the formula (II)

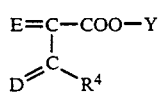

(II)

in which $R^4$ and Y have the abovementioned meanings,

D stands for oxygen and

E in this case stands for two hydrogen atoms, directly or optionally after isolation of the obtained benzylidene derivatives are reacted with aminocrotonic acid derivatives of the general formula (IV)

$$R^3-C=CH-R^2$$
$$\,\,\,\,\,\,\,\,\,|$$
$$\,\,\,\,\,\,NH_2$$

(IV)

in which $R^2$ and $R^2$ have the abovementioned meanings, or by a process in which

[B] aldehydes of the general formula (III)

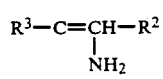

(III)

in which $R^1$ has the abovementioned meaning, are reacted with compounds of the general formula (V)

(V)

in which $R^2$ and $R^3$ have the abovementioned meanings, directly or after isolation of the obtained benzylidene derivatives of the general formula (VI)

(VI)

in which $R^1$, $R^2$ and $R^3$ have the abovementioned meanings, are reacted with compounds of the general formula (II)

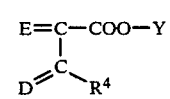

(IIa)

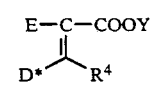

(IIb)

in which $R^4$ and Y have the abovementioned meanings,

D stands for NH,

D* stands for $NH_2$ and

E stands for one or two hydrogen atoms.

Depending on the type of starting materials used, the synthesis variants for the compounds according to the invention can be represented by the following equations:
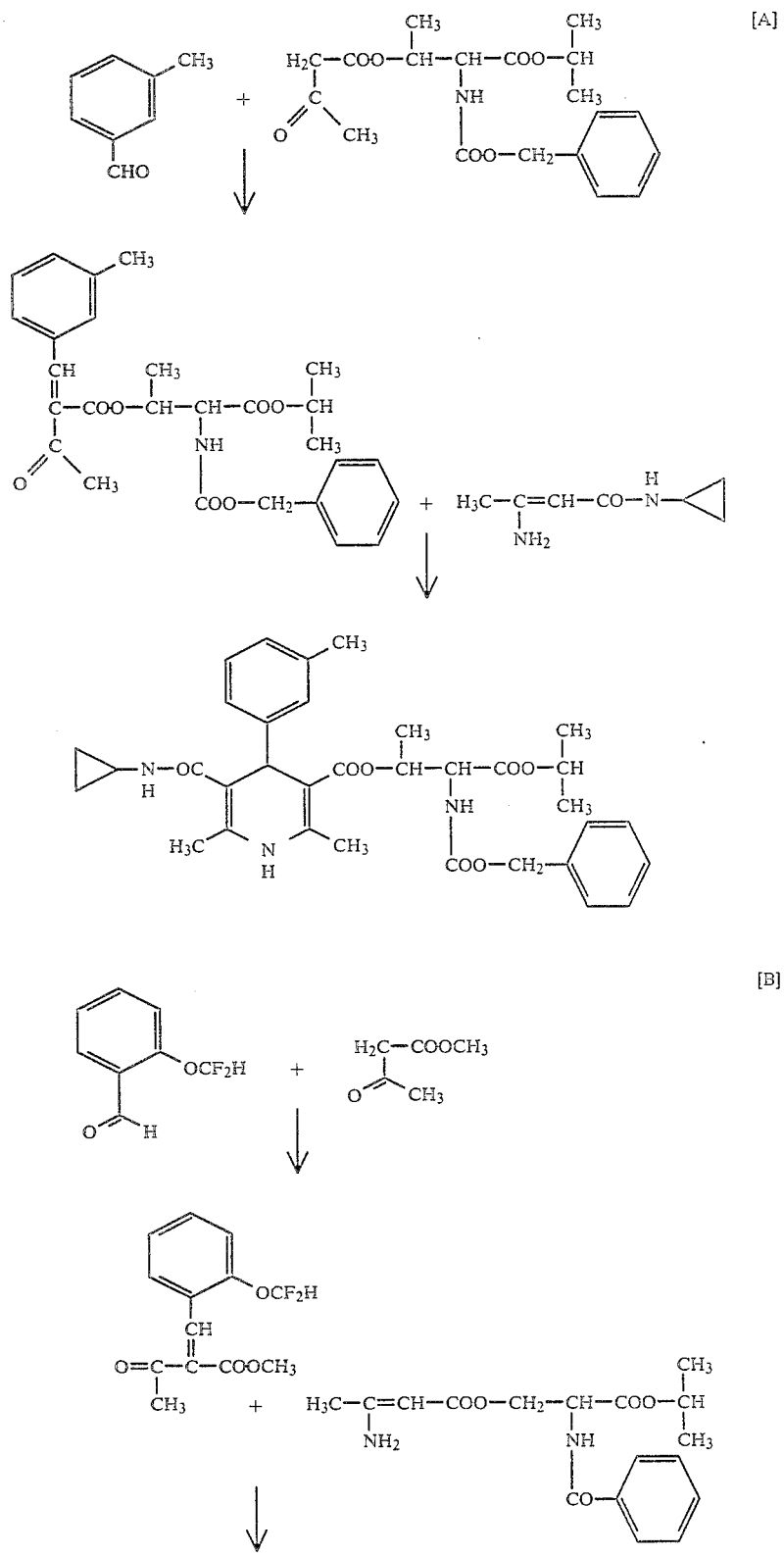

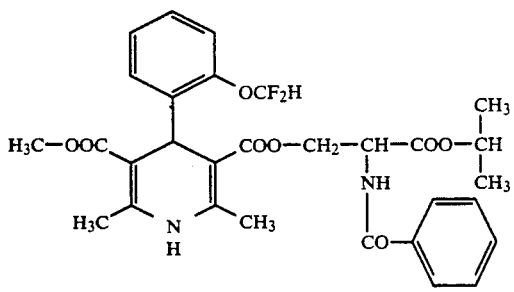

Suitable solvents for the process variants A and B are water and all inert organic solvents which do not change under the reaction conditions. These preferably include alcohols such as methanol, ethanol, propanol, isopropanol, ethers such as diethyl ether, dioxane, tetrahydrofuran, glycol monomethyl ether or glycol dimethyl ether, or amides such as dimethylformamide, dimethylacetamide or hexamethylphosphoric triamide, or glacial acetic acid, dimethyl sulphoxide, acetonitrile or pyridine, and hydrocarbons such as toluene, xylene or benzene.

The reaction temperatures can be varied within a relatively large range. In general, the reaction is carried out between $+10°$ C. and $+150°$ C., preferably between $+20°$ C. and $+100°$ C., in particular at the boiling point of the respective solvent.

The reaction can be carried out at atmospheric pressure, but also at elevated or reduced pressure. In general, the reaction is carried at atmospheric pressure.

When carrying out the process variants A and B according to the invention, the ratio of the substances participating in the reaction is arbitrary. However, in general the reaction is carried out using molar amounts of the reactants. The isolation and purification of the substances according to the invention is preferably carried out in such a way that the solvent is distilled off in vacuo and the residue, which may initially be obtained crystalline only after ice cooling, is recrystallized from a suitable solvent. In some cases, it may be necessary to purify the compounds according to the invention by chromatography.

The compounds of the general formula (II) are new. Only L-(2-benzyloxycarbonyl-2-tert.-butoxy-carbonyl-1-methyl)-ethyl 3-oxobutanoate is employed as a protecting group in the synthesis of amino acids [cf. Bull. Chem. Soc. Jpn. 52 (16), 3111–3112].

The invention therefore also relates to the starting materials of the general formula (II), in which $R^4$, Y, D and E have the abovementioned meanings, with the proviso that Y cannot be tert.-butyl if $R^4$ denotes methyl, D denotes oxygen and E denotes two hydrogen atoms. The new compounds of the formula (II) can be obtained by various processes. For example compounds in which
$R^4$ stands for methyl,
D stands for oxygen,
E stands for two hydrogen atoms, and
Y has the abovementioned meaning,
can be prepared by a process in which
[A] compounds of the general formula (VIII)

HO—Y (VIII)

in which

Y has the abovementioned meaning,
are reacted with diketene of the general formula (IX)

The compounds of the formula (II) in which
$R^4$ and Y have the abovementioned meanings,
D stands for oxygen and
E stands for two hydrogen atoms,
can alternatively be prepared by a process in which
[B] compounds of the formula (VIII) are reacted with compounds of the general formula (X)

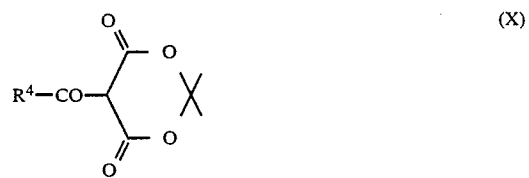

in which
$R^4$ has the abovementioned meaning.
The compounds of the general formula (II) in which
$R^4$ and Y have the abovementioned meanings,
D stands for NH, $D^*$ stands for $NH_2$ and
E stands for one or two hydrogen atoms,
are obtained by a process in which
[C] compounds of the general formula (II)
in which
$R^4$ and Y have the abovementioned meanings,
D stands for oxygen, and
E stands for one or two hydrogen atoms,
are reacted with ammonia.
[D] Compounds of the general formula (II)
in which
$R^4$ and Y have the abovementioned meanings,
D denotes oxygen and
E stands for the group $R^1$—CH=,
are obtained by a process in which
compounds of the general formula (III)
in which $R^1$ has the abovementioned meaning, are reacted with compounds of the general formula (II) in which
$R^4$ and Y have the abovementioned meanings,
D stands for oxygen and
E stands for one or two hydrogen atoms.

The aldehydes of the general formula (III) employed as starting materials are known or can be prepared by known methods [DOS (German Published Specification) Nos. 2,165,260; 2,401,665; T. D. Harris, G. P.

Roth, J. Org. Chem. 44, 2004 (1979); W. J. Dale, H. E. Hennis, J. Am. Chem. Soc. 78, 2543 (1956); Chem. Abstr. 59, 13929 (1963)].

The enamines of the general formula (IV) employed as starting materials are known or can be prepared by known methods [DOS (German Published Specification) No. 2,228,377; F. A. Glickman, A. C. Cope, J. Am. Chem. Soc. 67, 1017 (1945)].

The ylidene-β-ketocarboxylic acid derivatives of the general formula (VI) employed as starting materials are known or can be prepared by known methods [G. Jones "The Knoevenagel Condensation" in Organic Reactions Vol. XV, 204 (1967)].

The starting materials of the formula (VIII) are in some cases known or can be prepared by known methods [cf. Houben-Weyl, Methoden der organischen Chemie (Methods of Organic Chemistry), Volume 15, part 1, E. Wünsch, page 46 et seq.].

The compound of the formula (IX) and its reactions are known [cf. R. J. Clemens, Chem. Rev. 88, 241 (1986)].

The compounds of the formula (X) are known in some cases or can be prepared by customary methods [cf. J. Org. Chem. 43, 1087 (1978)].

The compounds of the general formula (I) can exist both as mixtures of diastereomers and as pure diastereomers. If pure L- or D-compounds are employed as starting materials of the formula (VIII), in the end pairs of diastereomers of the formula (I) are obtained from these, which, if desired, surprisingly can be easily resolved into the pure diastereomers by known methods such as column chromatography, fractional crystallization or Craig partition. [For Craig partition see, for example, "Verteilungsverfahren im Laboratorium ("Partition Methods in the Laboratory"), E. Hecker, Verlag Chemie GmbH, Weinheim, Bergstrasse (1955)].

This invention in addition relates to the use of compounds of the general formula (I) for the preparation of dihydropyridinecarboxylic acids of the general formula (XI)

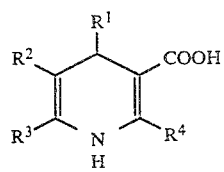

in which $R^1$, $R^2$, $R^3$ and $R^4$ have the abovementioned meaning, and their use as intermediates to make enantiomers of dihydropyridines, because surprisingly it has been found that the radical Y of the compounds of the formula (I) can be eliminated exceedingly easily compared to the customary known dihydropyridine esters. If pure diastereomers of the formula (I) are employed, pure enantiomeric carboxylic acids of the formula (XI) are obtained, which can be transformed by usual methods into esters, amides, nitriles, lactones etc. Hereby the pure enantiomeres of dihydropyridines can be easily obtained.

PREPARATION EXAMPLES

Example 1

(With separation of diastereomeres)

(1R,2S)-[1-Methyl-2-methoxycarbonyl-2-(4-tolyl-sulphamoyl)]-ethyl 1,4-dihydro-2,6-dimethyl-3-nitro-4-phenylpyridine-5-carboxylate

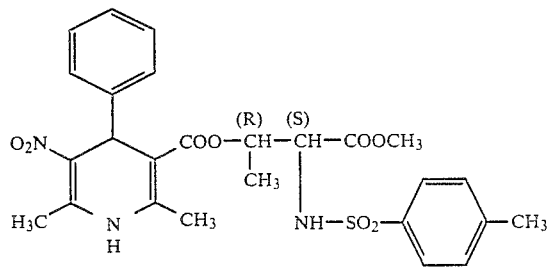

725 mg (3.8 mmol) of benzylidenenitroacetone are boiled for 3 hours with 1.4 g (3.8 mmol) of (1R,2S)-[1-methyl-2-methoxycarbonyl-2-(4-tolylsulphamoyl)]-ethyl β-aminocrotonate in 7 ml of ethanol. The mixture is concentrated and the two diastereomers are separated by column chromatography.

0.6 g of a yellow-coloured diastereomer of $R_f$=0.18 and 0.4 g of a diastereomer of $R_f$=0.146 are obtained.

TLC: silica gel aluminium roll, silica gel 60, F 254, layer thickness 0.2 mm (Merck)

Mobile phase: methylene chloride/ethyl acetate in the volume ratio 20:1.

Example 2

(With separation of diastereomeres)

Methyl (1R,2S)-[1-methyl-2-methoxycarbonyl-2-(4-tolylsulphamoyl)]-ethyl 1,4-dihydro-2,6-dimethyl-4-(3-nitrophenyl)-pyridine-3,5-dicarboxylate

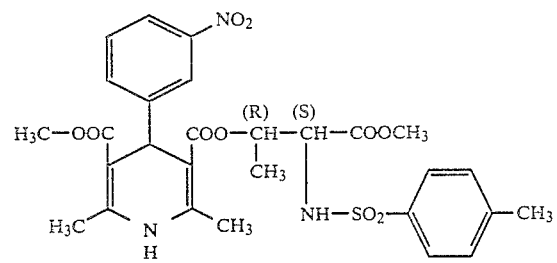

5 g (20 mmol) of methyl 2-(3-nitrobenzylidene)-3-oxo-butyrate are boiled for 5 hours with 7.4 g (20 mmol) of (1R,2S)-[1-methyl-2-methoxy-2-(4-tolylsulphamoyl)]-ethyl β-aminocrotonate in 40 ml of isopropanol. The mixture is cooled, and the deposited crystals are filtered off with suction and washed with isopropanol. 4.8 g (39.9% of theory) of a pure diastereomer of melting point: 157°–159° C. are obtained (see Example 4). $[\alpha]_{589}^{20}$= +49.3° (c=1.0:DMF).

Example 3

(1R,2S)-(1-Methyl-2-methoxycarbonyl-2-phenyl-carbamoyl)-ethyl 1,4-dihydro-2,6-dimethyl-3-nitro-4-phenyl-pyridine-5-carboxylate

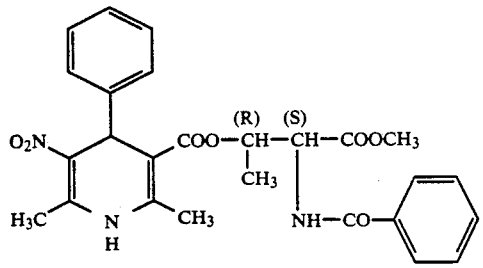

0.37 g (1.95 mmol) of benzylidene-nitroacetone are boiled in 4 ml of ethanol for 3 hours with 0.6 g (1.95 mmol) of (1R,2S)-(1-methyl-2-methoxycarbonyl-2-phenyl-carbamoyl)-ethyl β-aminocrotonate. The mixture is concentrated and the mixture of diastereomers is purified over a silica gel column using toluene/ethyl acetate. 0.7 g of a reddish yellow oil of $R_f$ 0.1 are obtained (mobile phase: methylene chloride/ethyl acetate 20:1).

Example 4

(With separation of diastereomeres)

Methyl (1R,2S)-1-methyl-2-methoxy-carbonyl-2-(p-tolylsulphamoyl)-ethyl 1,4-dihydro-2,6-dimethyl-4-(3-nitrophenyl)-pyridine-3,5-dicarboxylate 3.6 g (29.9% of theory) of the other diastereomer are obtained from the mother liquor of the compound from Example 2 as an oil by column chromatography. $R_f$: 0.38 Mobile phase: toluene/acetone (4:1)

Example 5

(Enantiomere acid)

1,4-Dihydro-2,6-dimethyl-3-methoxycarbonyl-4-(3-nitrophenyl)-pyridine-5-carboxylic acid

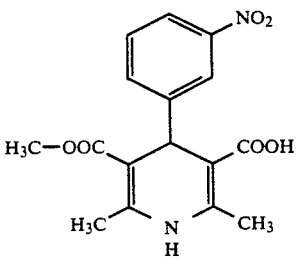

1.22 ml (8.15 mmol) of diaza-bicyclo-undecane are added to 2 g (3.33 mmol) of the compound from Example 2 in 18 ml of methanol and the mixture is stirred at room temperature for 3 hours. It is concentrated, water is added to the residue from the evaporation and the mixture is rendered acidic with 10% strength hydrochloric acid added dropwise with stirring. The deposited solid product is filtered off with suction, washed with water and then with ether. 1.02 g (88.5% of theory) of a colourless product of melting point 181°-182° C. with decomposition are obtained.

$[\alpha]_{589}^{20} = -21°$ (c=0.711, acetone) (exceed of enantiomeres (ee)>99%).

The compounds shown in the table below were obtained analogously to Examples 1 to 4.

Structural formula (header for table):

$$\begin{array}{c} R^1 \\ | \\ \text{(dihydropyridine ring with COO-Y at 3-position, CH}_3\text{ at 2 and 6, } R^2 \text{ at 5, NH)} \end{array}$$

The compounds have the general structure:
- Dihydropyridine core with N–H
- 2-CH$_3$, 6-CH$_3$
- 3-COO–Y
- 4-R$^1$
- 5-R$^2$

| Example No. | R$^1$ | R$^2$ | Y | M.p. [°C] | R$_f$ (Mobile phase) |
|---|---|---|---|---|---|
| 6 | C$_6$H$_4$–OCF$_2$H | NO$_2$ | (a)*–CH(CH$_3$)–CH(NH–COO–CH$_2$–C$_6$H$_5$)–COOCH$_3$ | — | (*1) 0.43/0.49 |
| 7 | C$_6$H$_4$–OCF$_2$H | NO$_2$ | (a)*–CH(CH$_3$)–CH(NH–SO$_2$–C$_6$H$_4$–CH$_3$)–COOCH$_3$ | oil 175–178 | (*1) 0.42 |
| 8 | C$_6$H$_4$–OCF$_2$H | NO$_2$ | (a)*–CH(CH$_3$)–CH(NH–COO–CH$_2$–C$_6$H$_5$)–COO–CH(CH$_3$)$_2$ | 115–118 | (*2) 0.56 |
| 9 | C$_6$H$_4$–OCF$_2$H | NO$_2$ | (a)*–CH(CH$_3$)–CH(NH–COO–C(CH$_3$)$_3$)–COO–CH(CH$_3$)$_2$ | oil | (*2) 0.46 |
| 10 | C$_6$H$_4$–OCF$_2$H | NO$_2$ | (a)*–CH(CH$_3$)–CH(NH–CO–C$_6$H$_5$)–COO–CH(CH$_3$)$_2$ | foam | (*2) 0.36/0.41 |

-continued

Structure:

$$\begin{array}{c} \text{R}^2\text{-substituted dihydropyridine with COO-Y at 3-position, R}^1 \text{ at 4-position,} \\ \text{CH}_3 \text{ groups at 2 and 6, NH in ring} \end{array}$$

| Example No. | R¹ | R² | Y | M.p. [°C.] | $R_f$/(Mobile phase) |
|---|---|---|---|---|---|
| 11 | phenoxymethyl-phenyl (C₆H₅-O-CH₂-C₆H₄-) | H₃C—OOC | (a)* —CH(CH₃)—CH(NH—COO—CH₂—C₆H₅)—COOCH₃ | oil | (*2) 0.2/0.24 (*1) 0.54/0.59 |
| 12 | phenoxymethyl-phenyl | H₃C—OOC | (a)* —CH(CH₃)—CH(NH—SO₂—C₆H₄-CH₃)—COOCH₃ | 158–160 | (*2) 0.38/0.41 (*1) 0.53/0.59 |
| 13 | 4-OCF₂H-phenyl | NO₂ | (a)* —CH(CH₃)—CH(NH₂)—COO—CH(CH₃)₂ | foam | (*2) 0.02/0.04 (*3) 0.31 |
| 14 | 4-OCF₃-phenyl | NO₂ | (a)* —CH(CH₃)—CH(NH—SO₂—C₆H₄-CH₃)—COOCH₃ | 178 | (*4) 0.16/0.21 |
| 15 | 4-CH₃-phenyl | NO₂ | (a)* —CH(CH₃)—CH(NH—SO₂—C₆H₄-CH₃)—COOCH₃ | oil | (*4) 0.16/0.19 |

-continued

Structure:
$$\begin{array}{c}\text{COO-Y}\\ R^1\\ R^2\\ H_3C\quad N\quad CH_3\\ H\end{array}$$

| Example No. | R¹ | R² | Y | M.p. [°C.] | R_f/(Mobile phase) |
|---|---|---|---|---|---|
| 16 | 4-(OCF₂H)-phenyl | NO₂ | (a)*—CH(CH₃)—CH(NH—CO—O-phenyl)—COOCH₃ | oil | (*4) 0.09 |
| 17 | 4-NO₂-phenyl | NO₂ | (a)*—CH(CH₃)—CH(NH—SO₂-(4-CH₃-phenyl))—COOCH₃ | oil | (*4) 0.29/0.36 |
| 18 | 4-F-phenyl | NO₂ | (a)*—CH(CH₃)—CH(NH—SO₂-(4-CH₃-phenyl))—COOCH₃ | 176-182 | (*4) 0.22/0.92 (*1) 0.22/0.29 |
| 19 | 4-phenoxy-benzyl | H₃C—OOC | (a)*—CH(CH₃)—CH(NH—COO—C(CH₃)₃)—COOCH₃ | oil | (*2) 0.24/0.29 (*1) 0.56/0.62 |
| 20 | 4-phenoxy-benzyl | H₃C—OOC | (a)*—CH(CH₃)—CH(NH—CO—O-phenyl)—COOCH₃ | foam | (*2) 0.394/0.44 (*1) 0.54/0.59 |

-continued

Structure:

$$\begin{array}{c} R^1 \\ | \\ \text{dihydropyridine with } R^2, COO-Y, CH_3, H_3C, \text{ NH} \end{array}$$

The parent structure shows a 1,4-dihydropyridine: position 3 has COO—Y, position 5 has R², position 4 has R¹, positions 2 and 6 have CH₃, and N—H.

| Example No. | R¹ | R² | Y | M.p. [°C] | R_f (Mobile phase) |
|---|---|---|---|---|---|
| 21 | C₆H₅—O—CH₂—C₆H₅ (phenoxymethyl-phenyl) | H₃C—OOC | (a)* —CH(CH₃)—CH(NH₂)—COO—CH₃ | oil | (*2) (*1) 0.07/0.21 |
| 22 | C₆H₅—O—CH₂—C₆H₅ | H₃C—OOC | (a)* —CH(CH₃)—CH(NH—SO₂—C₆H₄—NO₂)—COOCH₃ | oil | (*1) 0.63/0.66 (*2) 0.4 |
| 23 | C₆H₅—O—C₆H₄—OCF₂H | NO₂ | (a)* —CH(CH₃)—CH(NH—SO₂—C₆H₄—NO₂)—COOCH₃ | 199–202 | (*1) 0.55 |
| 24 | C₆H₅—O—CH₂—C₆H₅ | H₃C—OOC | (a)* —CH(CH₃)—CH(NH—CO—C₆H₄—NO₂)—COOCH₃ | oil | (*5) 0.53/0.59 (*1) 0.89 |
| 25 | C₆H₅—O—CH₂—C₆H₅ | H₃C—OOC | (a)* —CH(CH₃)—CH(NH—COO—CH₃)—COO—CH₃ | oil | (*1) 0.44 (*2) 0.18 |

-continued

[Structure: dihydropyridine core with R¹, R², COO-Y, CH₃, CH₃, N-H substituents]

| Example No. | R¹ | R² | Y | M.p. [°C.] | R_f/(Mobile phase) |
|---|---|---|---|---|---|
| 26 | C₆H₅-O-CH₂- (phenoxymethyl) | H₃C-OOC | (a)* -CH(CH₃)-CH(COOCH₃)-NH-SO₂-CH₃ | oil | (*1) 0.43 (*2) 0.18/0.23 |
| 27 | C₆H₅-O-CH₂- | H₃C-OOC | (a)* -CH(CH₃)-CH(COOCH₃)-NH-CO-CH₃ | oil | (*1) 0.17/0.22 (*3) 0.27/0.32 |
| 28 | C₆H₅-O-CH₂- | H₃C-OOC | (a)* -CH(CH₃)-CH(COOCH₃)-NH-SO₂-C₆H₄-Cl (4-Cl) | oil | (*6) 0.42/0.46 |
| 29 | C₆H₅-O-CH₂- | H₃C-OOC | (a)* -CH(CH₃)-CH(COO-C₆H₅)-NH-SO₂-CH₃ | oil | (*6) 0.32/0.36 |
| 30 | C₆H₅-O-CH₂- | cyclopropyl-CO-NH- | (a)* -CH(CH₃)-CH(COOCH₃)-NH-SO₂-C₆H₄-CH₃ (4-CH₃) | oil | (*3) 0.46/0.32 |

-continued

[Structure: dihydropyridine with R¹ at 4-position, R² at 5-position, COO-Y at 3-position, CH₃ at 2 and 6 positions, NH in ring]

| Example No. | R¹ | R² | Y | M.p. [°C] | R_f (Mobile phase) |
|---|---|---|---|---|---|
| 31 | phenoxymethyl-phenyl (C₆H₅-O-CH₂-C₆H₄-) | cyclopropyl-CO-NH- | (a)*-CH(CH₃)-CH(COOCH₃)-NH-SO₂-C₆H₅ | foam | (*7) 0.44/0.5 (*3) 0.35/0.4 |
| 32 | phenoxymethyl-phenyl | cyclopropyl-CO-NH- | (a)*-CH(CH₃)-CH(COOCH₃)-NH-SO₂-C₆H₄-NO₂ | foam | (*7) 0.59/0.65 (*3) 0.49/0.55 |
| 33 | (OCF₂H)-phenyl | NO₂ | (a)*-CH(CH₃)-CH(COOCH₃)-NH-SO₂-C₆H₅ | 194–197 | (*2) 0.45 |
| 34 | phenoxymethyl-phenyl | cyclopropyl-CO-NH- | (a)*-CH(CH₃)-CH(COOCH₃)-NH-CO-C₆H₅ | foam | (*2) 0.02 (*3) 0.42 |
| 35 | (OCF₂H)-phenyl | NO₂ | (a)*-CH(CH₃)-CH(COOCH₃)-NH-CO-C₆H₄-NO₂ | foam | (*1) 0.39 |

-continued

[Structure: dihydropyridine with R¹, R², COO-Y, CH₃, and H₃C substituents, NH ring]

| Example No. | R¹ | R² | Y | M.p. [°C] | R_f (Mobile phase) |
|---|---|---|---|---|---|
| 36 | 4-(OCF₂H)-C₆H₄- | NO₂ | (a)* —CH(CH₃)—CH(COOCH₃)—(4-Cl-C₆H₄)NH—SO₂— | 180 | (*2) 0.55 |
| 37 | 4-(OCF₂H)-C₆H₄- | NO₂ | (a)* —CH(CH₃)—CH(COOCH₃)—NH—SO₂—CH₃ | oil | (*1) 0.26 |
| 38 | C₆H₅-O-CH₂-C₆H₄- | H₃C—OOC | (a)* —CH(CH₃)—CH(COOCH₃)—(3,5-(NO₂)₂-C₆H₃)NH—CO— | 157–159 | (*1) 0.29/0.33 (*8) 0.39/0.47 |
| 39 | C₆H₅-O-CH₂-C₆H₄- | H₃C—OOC | (a)* —CH(CH₃)—CH(COO—CH(CH₃)₂)—(4-NO₂-C₆H₄)NH—SO₂— | foam | (*4) 0.37/0.41 |
| 40 | C₆H₅-O-CH₂-C₆H₄- | H₃C—OOC | (a)* —CH(CH₃)—CH(COO—CH(CH₃)₂)—(4-CH₃-C₆H₄)NH—SO₂— | foam | (*1) 0.67 (*9) 0.18 |

-continued $$\begin{array}{c} \text{COO-Y} \\ R^1 \diagup \diagdown \diagup CH_3 \\ | \phantom{xxx} | \\ R^2 \diagdown \diagup \diagdown N \diagup CH_3 \\ H \end{array}$$

| Example No. | R¹ | R² | Y | M.p. [°C] | R_f (Mobile phase) |
|---|---|---|---|---|---|
| 41 | phenoxymethyl-phenyl | H₃C—OOC | (a)* —CH(CH₃)—CH—COO—CH(CH₃)₂ — NH—CO—(3,5-dinitrophenyl) | foam | (*2) 0.76/0.82 |
| 42 | phenoxymethyl-phenyl | cyclopropyl-HN—OC | (a)* —CH(CH₃)—CH—COO—CH₃ — NH—CO—(3,5-dinitrophenyl) | 155–157 | (*3) 0.58/0.64 (*10) 0.47/0.52 |
| 43 | phenoxymethyl-phenyl | H₅C₂—HN—OC | (a)* —CH(CH₃)—CH—COOCH₃ — NH—CO—(3,5-dinitrophenyl) | 118–122 | (*2) 0.05 (*3) 0.71 |
| 44 | phenoxymethyl-phenyl | H₅C₂—HN—OC | (a)* —CH(CH₃)—CH—COO—CH₃ — NH—SO₂—(4-methylphenyl) | | (*7) 0.43/0.5 (*3) 0.46/0.52 |

-continued

| Example No. | R¹ | R² | Y | M.p. [°C] | R_f (Mobile phase) |
|---|---|---|---|---|---|
| 45 | phenyl-OCF₂H | NO₂ | (b)* —CH(CH₃)—CH(COO—CH₃)—NH—SO₂—C₆H₄—CH₃ | 178 | (*9) 0.48 |
| 46 | phenyl-OCF₃ | NO₂ | (b)* —CH(CH₃)—CH(COO—CH₃)—NH—SO₂—C₆H₄—CH₃ | 186–188 | (*2) 0.56 |
| 47 | phenyl-Cl | γ-butyrolactone (3,4-dimethyl) | (a)* —CH(CH₃)—CH(COO—CH₃)—NH—SO₂—C₆H₄—CH₃ | >270 | |
| 48 | 2-benzyloxyphenyl | —COOCH₃ | (a)* —CH(CH₃)—CH(COOCH₃)—NH—CO—NH—C₆H₅ | oil | (*2) 0.13 / 0.17 |
| 49 | 2-nitrophenyl | —COOCH₃ | (a)* —CH(CH₃)—CH(COOCH₃)—NH—SO₂—C₆H₄—CH₃ | oil | (*1) 0.35 |

Core structure: 1,4-dihydropyridine with 2,6-dimethyl, 3-COO-Y, 4-R¹, 5-R², N-H

-continued

| Example No. | R¹ | R² | Y | M.p. [°C.] | R_f (Mobile phase) |
|---|---|---|---|---|---|
| 50 | 3-NO₂-phenyl | −COO−CH(CH₃)₂ | (a)* −CH(CH₃)−CH(NHSO₂-p-tolyl)−COOCH₃ | oil | (*1) 0.54 |
| 51 | 2-(phenylmethoxy)phenyl | −COO−(CH₂)₂−N(CH₃)−CH₂−phenyl | (a)* −CH(CH₃)−CH(NHSO₂-p-tolyl)−COOCH₃ | oil | (*1) 0.33 |
| 52 | 2-NO₂-phenyl | −COO−(CH₂)₂−N(CH₃)−CH₂−phenyl | (a)* −CH(CH₃)−CH(NHSO₂-p-tolyl)−COOCH₃ | oil | (*1) 0.16 |
| 53 | 3-NO₂-phenyl | −COO−CH₂−CH₂−O−CH₃ | (a)* −CH(CH₃)−CH(NHSO₂-p-tolyl)−COOCH₃ | oil | (*1) 0.38/0.42 |
| 54 | 2-OCF₂H-phenyl | −NO₂ | (b)* −CH(CH₃)−CH(NH−COO−C(CH₃)₃)−COOCH₃ | oil | 0.56/0.6 |

(a = R, S; b = S, R)

Intermediate No. 1

(1R,2S)-(2-Benzyloxycarbamoyl-2-methoxycarbonyl-1-methyl)-ethyl acetoacetate

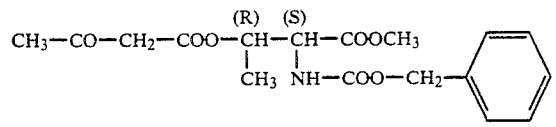

(a) Preparation of methyl (2S,3R)-2-amino-3-hydroxybutyrate 109 ml (1.5 mol) of thionyl chloride are added dropwise at 0° C. with strong cooling to 240 ml of methanol. 60 g (0.5 mol) of L-threonine are then added and the mixture is stirred at room temperature for 2 days, a clear solution resulting. After concentration, 85 g of a colorless oil are obtained.

(b) Preparation of methyl (2S,3R)-2-benzyloxycarbonylamino-3-hydroxybutyrate 34.1 g (0.201 mol) of methyl (2S,3R)-2-amino-3-hydroxybutyrate are mixed in 300 ml of ethyl acetate with a solution of 40 g of potassium carbonate in 200 ml of water. 33 ml (0.215 mol) of 90% strength benzyloxycarbonyl chloride are then added dropwise at 0° C. The mixture is stirred at 0°–5° C. for 2 hours and separated, and the ethyl acetate phase is washed twice with water, dried and concentrated. Hexane is added to the crystals obtained and filtered off with suction. 42.2 g (78.6%) of colorless crystals of melting point 96° C. are obtained.

0.2 ml of triethylamine is added to 35 g (0.13 mol) of methyl (2S,3R)-2-benzyloxycarbonylamino-3-hydroxybutyrate in 75 ml of absolute toluene. 9.8 ml (0.13 mmol) of diketene, dissolved in 10 ml of absolute toluene, are added dropwise at 90° C., the temperature being kept between 90° C. and 98° C. The mixture is subsequently stirred at 95° C. for 2 hours, cooled, shaken once with water, dried and concentrated. 44.3 g (96.6% of theory) of a brown-colored oil are obtained.

Intermediate No. 2

(1R,2S)-[1-methyl-2-methoxycarbonyl-2-(4-nitrophenylsulphamoyl)]-ethyl 3-imino-acetoacetate or (1R,2S)-[1-methyl-2-methoxycarbonyl-2-(4-nitrophenylsulphamoyl)]-ethyl β-aminocrotonate

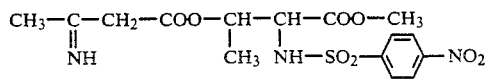

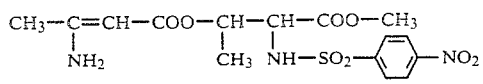

200 mg of p-toluenesulphonic acid are added to 39.2 g (97.5 mmol) of (1R,2S)-[1-methyl-2-methoxycarbonyl-2-(4-nitrophenylsulphamoyl)]-ethyl acetoacetate in 370 ml of toluene and the mixture is boiled in a water separator for 4 hours, ammonia being introduced at the same time. The mixture is cooled, shaken twice with water, dried and concentrated. The crystals obtained are stirred with a little ethanol, filtered off with suction and washed with ethanol and ether. 20.2 g of beige-colored crystals of melting point 155°–156° C. are obtained.

Intermediate No. 3

(1R,2S)-[1-Methyl-2-methoxycarbonyl-2-(3,5-dinitrophenylcarbamoyl)]-ethyl 2-(2-benzyloxybenzylidene)-3-oxo-butyrate

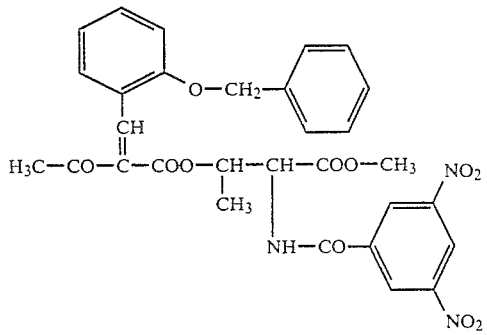

100 g (243.5 mmol) of (1R,2S)-[1-methyl-2-methoxycarbonyl-2-(3,5-dinitrophenylcarbamoyl)]-ethyl acetoacetate are stirred in 300 ml of isopropanol with 51.3 g (243.5 mmol) of 2-benzyloxybenzaldehyde. A freshly prepared solution of 1.5 ml of piperidine and 0.75 ml of acetic acid in 12 ml of isopropanol is added to this suspension. The mixture is stirred at 40°–45° C. for 4 hours, a non-crystalline magma being formed initially and crystallization then occurring. The crystals are filtered with suction and washed with isopropanol and ether. 123.6 g (83.9% of theory) of a pale brown product of melting point 143°–146° C. are obtained.

The intermediates shown in the table below were obtained analogously to the directions for intermediates No. 1 to 3.

| Intermediate Example No. | B | $R^{13}$ | $R^{14}$ | M.p.: $R_f$ | Configuration (*1) (1); (2) |
|---|---|---|---|---|---|
| | | $H_3C-\underset{\underset{O}{\|\|}}{C}-CH_2-COO-\overset{(1)}{CH}-\overset{(2)}{CH}-COOR^{13}$ | | | |
| | | | $\underset{CH_3}{\|}\ \underset{B-R^{14}}{\|}$ | | |
| 4 | NH—COO— | —CH₃ | —C(CH₃)₃ | oil, 0.6 | R,S |
| 5 | NH—COO— | —CH(CH₃)₂ | —C(CH₃)₃ | oil, 0.62 | R,S |

-continued

| No. | | | | | |
|---|---|---|---|---|---|
| 6 | NH—COO— | —CH(CH₃)₂ | —CH₂—C₆H₅ 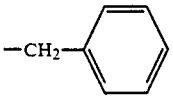 | oil, 0.7 | R,S |
| 7 | NH—SO₂— | —CH₃ | 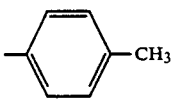 p-tolyl | 85° | R,S |
| 8 | NH—CO— | —CH(CH₃)₂ |  phenyl | oil, 0.61 | R,S |
| 9 | NH—CO— | —CH₃ |  phenyl | oil, 0.5 | R,S |
| 10 | NH—SO₂— | —CH₃ | 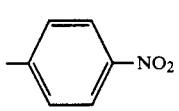 p-NO₂-phenyl | at 78° C. | R,S |
| 11 | NH—CO— | —CH₃ | 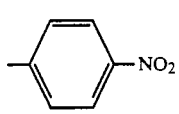 p-NO₂-phenyl | at 84° C. | R,S |
| 12 | NH—COO— | —CH₃ | —CH₃ | 70–72° C. | R,S |
| 13 | NH—SO₂— | —CH₃ | —CH₃ | oil, 0.29 | R,S |
| 14 | NH—CO— | —CH₃ | —CH₃ | oil, 0.31 | R,S |
| 15 | NH—SO₂— | —CH₃— | 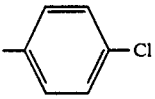 p-Cl-phenyl | 95–96° C. | R,S |
| 16 | NH—SO₂— | —CH₃ |  phenyl | 105–106° C. | R,S |
| 17 | NH—CO— | —CH₃ | 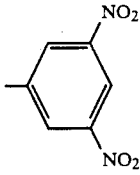 2,4-dinitrophenyl | 79–84° C. | R,S |
| 18 | NH—SO₂— | —CH(CH₃)₂ | 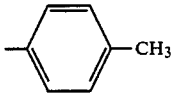 p-tolyl | 100° C. | R,S |
| 19 | NH—CO— | —CH(CH₃)₂ | 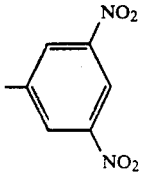 2,4-dinitrophenyl | 162–165° C. | R,S |
| 20 | NH—SO₂— | —CH₃ | 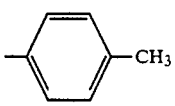 p-tolyl | 99–100° C. | S,R |

-continued

| # | | | | | |
|---|---|---|---|---|---|
| 21 | NH—CO— | —CH$_3$ | 3,5-dinitrophenyl | 83° C. | S,R |
| 22 | NH—SO$_2$— | —CH(CH$_3$)$_2$ | 4-nitrophenyl | | R,S |
| 22a | —NH—CO—NH— | CH$_3$ | phenyl | | R,S |

$$H_3C-C-CH_2-COO-\overset{(1)}{CH}-\overset{(2)}{CH}-COOR^{13}$$
$$\underset{NH}{\|} \quad \underset{CH_3}{|} \quad \underset{B-R^{14}}{|}$$

| # | | | | | |
|---|---|---|---|---|---|
| 23 | NH—COO— | —CH$_3$ | —CH$_2$—phenyl | oil, 0.61 | R,S |
| 24 | NH—COO— | —CH$_3$ | —C(CH$_3$)$_3$ | 0.6 | R,S |
| 25 | NH—SO$_2$— | —CH$_3$ | 4-methylphenyl | 94–96° C. | R,S |
| 26 | NH—COO— | —CH(CH$_3$)$_2$ | —CH$_2$—phenyl | oil, 0.69 | R,S |
| 27 | NH—COO— | —CH(CH$_3$)$_2$ | —C(CH$_3$)$_3$ | 93–95° C. | R,S |
| 28 | NH—CO— | —CH(CH$_3$)$_2$ | phenyl | oil, 0.59 | R,S |
| 29 | NH—CO— | —CH$_3$ | phenyl | oil, 0.5 | R,S |
| 30 | NH—SO$_2$— | —CH$_3$ | 4-methylphenyl | 114–115° C. | S,R |
| 31 | NH—SO$_2$— | —CH$_3$ | 4-nitrophenyl | 152–155° C. | R,S |
| 32 | NH—CO— | —CH$_3$ | 4-nitrophenyl | 102–103° C. | R,S |
| 33 | NH—COO— | —CH$_3$ | —CH$_3$ | oil, 0.32 | R,S |
| 34 | NH—SO$_2$— | —CH$_3$ | —CH$_3$ | oil, 0.28 | R,S |
| 35 | NH—CO— | —CH$_3$ | —CH$_3$ | | R,S |

-continued
| | | | | M.p.: | Configuration |
|---|---|---|---|---|---|
| 36 | NH—SO$_2$— | —CH$_3$ | 4-Cl-C$_6$H$_4$— | 82–86° C. | R,S |
| 37 | NH—SO$_2$— | —CH$_3$ | C$_6$H$_5$— | 120° C. | R,S |
| 38 | NH—CO— | —CH$_3$ | 3,5-(NO$_2$)$_2$-C$_6$H$_3$— | 161–164° C. | R,S |
| 39 | NH—SO$_2$— | —CH(CH$_3$)$_2$ | 4-NO$_2$-C$_6$H$_4$— | 153–156° C. | R,S |
| 40 | NH—SO$_2$— | —CH(CH$_3$)$_2$ | 4-CH$_3$-C$_6$H$_4$— | 180–182° C. | R,S |
| 41 | NH—CO— | —CH(CH$_3$)$_2$ | 3,5-(NO$_2$)$_2$-C$_6$H$_3$— | 155–159° C. | R,S |
| Intermediate Example No. | B | E | R$^{14}$ | M.p.: R$_f$: | Configuration (1); (2) |
|---|---|---|---|---|---|
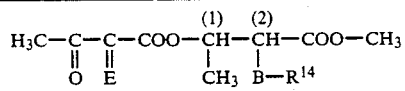
| 42 | NH—SO$_2$— | 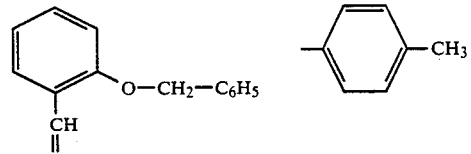 | 4-CH$_3$-C$_6$H$_4$— | oil, 0.8 | R,S |
| 43 | NH—CO— | 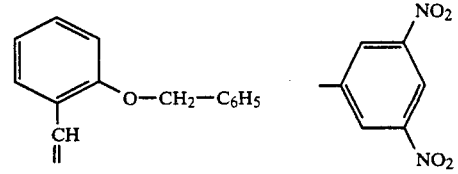 | 3,5-(NO$_2$)$_2$-C$_6$H$_3$— | 141° C. | S,R |
| 44 | NH—SO$_2$— | 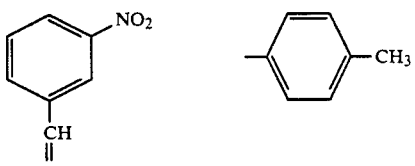 | 4-CH$_3$-C$_6$H$_4$— | oil | R,S |

-continued

| | | | | |
|---|---|---|---|---|
| 45 | NH—CO—NH— | 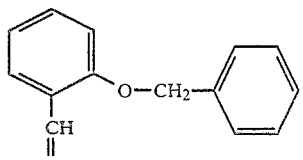 | 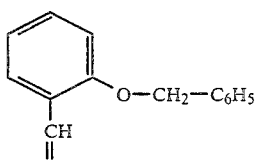 | R,S |
| 46 | NH—SO$_2$— | 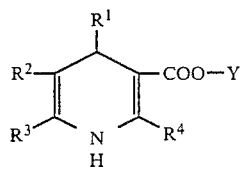 | 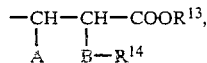 | oil, 0 8    S,R |

Explanation of symbols for the tables
(*1) Toluene/ethyl acetate 1:1
(*2) Methylene chloride/ethyl acetate 9:1
(*3) Methylene chloride/ethyl acetate 1:4
(*4) Methylene chloride/ethyl acetate 20:1
(*5) Chloroform/ethyl acetate 9:1
(*6) Toluene/ethyl acetate 2:1
(*7) Ethyl acetate
(*8) Toluene/methyl isobutyl ketone 3:1
(*9) Toluene/ethyl acetate 4:1
(*10) Toluene/ethyl acetate 1:5

It will be understood that the specification and examples are illustrative but not limitative of the present invention and that other embodiments within the spirit and scope of the invention will suggest themselves to those skilled in the art.

We claim:

1. A dihydropyridine compound of the formula $$\begin{array}{c} R^1 \\ R^2 \diagup\!\!\!\diagdown \!-\!COO\!-\!Y \\ R^3 \diagdown\!\!\!\diagup \\ \phantom{xx}N\phantom{xx}R^4 \\ \phantom{xx}H \end{array}$$

in which $R^1$ represents aryl having 6 to 10 carbon atoms which is monosubstituted, disubstituted or trisubstituted by identical or different nitro, cyano, $C_1$-$C_6$-halogenoalkyl, halogen, $C_1$-$C_6$-alkyl or $C_1$-$C_6$-alkoxycarbonyl, or by $C_1$-$C_6$ halogenoalkoxy, $C_1$-$C_4$-halogenoalkylthio, carbamoyl, dialkyl carbamoyl having up to 6 carbon atoms per alkyl group, or $C_2$-$C_8$-alkenyl which can optionally be substituted by $C_1$-$C_6$-alkoxycarbonyl or by phenylsulphonyloxy which is optionally substituted by $C_1$-$C_6$-alkyl, $C_1$-$C_6$-alkoxy, nitro, halogen, cyano, $C_1$-$C_4$-halogenoalkyl or $C_1$-$C_4$-halogenoalkoxy, or by $C_1$-$C_8$-alkyl-amino or dialkylamino each having up to 6 carbon atoms per alkyl group, or $C_1$-$C_8$-alkyl-amino or dialkylamino each having up to 6 carbon atoms per alkyl group, or $C_1$-$C_8$-acylamino, or by $C_1$-$C_8$-alkoxy or $C_1$-$C_8$-alkylthio, each of which can optionally be substituted by cyclohexyl or phenyl which, in turn, can be substituted by cyclohexyl or phenyl which, in turn, can be substituted by halogen, $C_1$-$C_6$-alkyl, $C_1$-$C_6$-alkoxy, nitro, $C_1$-$C_4$-halogenoalkyl, $C_1$-$C_2$-alkoxycarbonyl, cyano or $C_1$-$C_4$-halogenoalkoxy, $R^2$ represents a group of the formula COO—Z—$R^5$ wherein $R^5$ represents hydrogen, or represents a straight-chain, branched or cyclic, saturated or unsaturated hydrocarbon radical having up to 12 C atoms which can be interrupted by an oxygen or sulphur atom and which can be substituted by $NO_3$, hydroxyl, nitro, halogen, $C_1$-$C_6$-acyloxy, carboxyl, $C_1$-$C_6$-alkoxycarbonyl, CN or $C_1$-$C_8$-acyl, or by phenyl or phenoxy which are optionally substituted by halogen, $C_1$-$C_4$-alkyl, $C_1$-$C_4$-alkoxy or $C_1$-$C_2$-halogenoalkyl, Z-denotes a single bond or a straight-chain or branched alkylene chain having up to 10 C atoms, $R^3$ represents straight-chain, branched or cyclic alkyl having up to 6 carbon atoms which is optionally substituted by hydroxyl, cyano, phenyl, halogeno or aminoethoxy, $R^4$ represents straight-chain or branched alkyl or alkenyl having up to 12 carbon atoms and which can optionally be substituted by halogen, hydroxyl, $C_1$-$C_6$-alkoxy, trifluoromethyl, carboxyl, $C_1$-$C_6$-alkoxycarbonyl or phenyl which can be substituted by nitro, halogen, $C_1$-$C_2$-alkyl, $C_1$-$C_4$-alkoxy, trifluoromethyl or trifluoromethoxy, Y represents a radical $$\begin{array}{c} -CH-CH-COOR^{13}, \\ | \phantom{xx} | \\ A \phantom{xx} B-R^{14} \end{array}$$

wherein

A represents hydrogen or methyl,

B represents a group of the formula —NH, —NH—CO—, —NH—CS—, —NH—COO—, —NH—SO$_2$— or —NH—CO—NH— or —NH—CS—NH, $R^{13}$ represents for hydrogen, or stands for straight-chain or branched alkyl having up to 12 carbon atoms and which can be substituted by halogen, hydroxyl, carboxy, cyano, $C_1$-$C_8$-alkoxycarbonyl, carbonyl, alkylamino or dialkylamino having up to 8 carbon atoms, carbamoyl, $C_1$-$C_6$-alkoxy or phenyl which can be substituted by nitro, cyano, trifluoromethyl, trifluoromethoxy, halogen, $C_1$-$C_6$-alkyl, and $R^{14}$ represents hydrogen, or represents straight-chain or branched alkyl or alkenyl each having up to 12 carbon atoms and which can be substituted by halogen, hydroxyl, $C_1$-$C_8$-alkoxy, nitro, cyano, $C_1$-$C_8$-alkylthio, carboxyl, $C_1$-$C_8$-alkoxycarbonyl or phenyl which can be substituted by nitro, cyano, trifluoromethyl, trigluoromethoxy, $C_1$-$C_8$-alkyl, halogen or $C_1$-$C_8$-alkoxy or represents cycloalkyl having 3 to 8 carbon atoms, or represents aryl having 6 to 10 carbon atoms which can be monosubstituted to pentasubstituted by identical or different nitro, cyano, halogen, $C_1$-$C_8$-alkyl, $C_1$-$C_8$-alkoxy, $C_1$-$C_8$-alkylthio, carbamoyl or dialkylcarbamoyl in each case having up to 6 carbon atoms per alkyl group, carboxyl, $C_1$-$C_8$-alkoxycarbonyl, $C_1$-$C_6$-halogenoalkylthio, $C_1$-$C_6$-halogenoalkoxy, $C_1$-$C_6$-halogenoalkylthio, $C_1$-$C_6$-halogenoalkoxy, $C_1$-$C_6$-halogenoalkylthio, $C_1$-$C_6$-alkylsulphonyl, $C_1$-$C_6$-alkylsulphamoyl, amino, $C_1$-$C_8$-alkylamino or dialkylamino in each case having up to 8 carbon atoms per alkyl group or $C_1$-$C_8$-acylamino, or a physiologically acceptable salt thereof.

2. A compound according to claim 1, wherein such compound is methyl [1-methyl-2-methoxycarbonyl-2-(4-tolyl-sulphamoyl)]-ethyl 1,4-dihydro-2,6-dimethyl-4-(2-benzyloxy)-pyridine-3,5-dicarboxylate of the formula

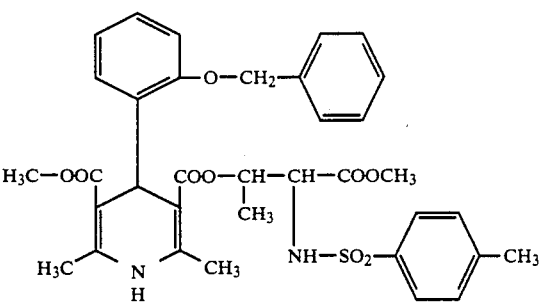

or a physiologically acceptable salt thereof.

3. A cardioactive composition comprising a cardioactive amount of a compound or salt thereof according to claim 1 and a pharmaceutically acceptable diluent.

4. A unit dose of a composition according to claim 3 in the form of a tablet, capsule or ampule.

5. A method of modifying the contractility of the heart of a patient in need thereof which comprises administering to such patient an amount effective therefor of a cardioactive amount of a compound or a salt thereof according to claim 1.

6. The method according to claim 5, wherein such compound is
methyl [1-methyl-2-methoxycarbonyl-2-(4-tolylsulphamoyl)]-ethyl 1,4-dihydro-2,6-dimethyl-4-(2-benzyloxy)-pyridine-3,5-dicarboxylate,
methyl [1-methyl-2-methoxycarbonyl-2-(4-nitrophenylcarbamoyl)]-ethyl 1,4-dihydro-2,6-dimethyl-4-(2-benzyloxy)-pyridine-3,5-dicarboxylate, or
methyl [1-methyl-2-methoxycarbonyl-2-(3,5-dinitrophenylcarbanitk)]-ethyl 1,4-dihydro-2,6-dimethyl-4-(2-benzyloxy)-pyridine-3,5-dicarboxylate.

* * * * *